US011691938B2

(12) United States Patent
Himmler et al.

(10) Patent No.: US 11,691,938 B2
(45) Date of Patent: Jul. 4, 2023

(54) PROCESS FOR PREPARING 2,6-DIALKYLPHENYLACETIC ACIDS

(71) Applicant: Bayer Aktiengesellschaft, Leverkusen (DE)

(72) Inventors: Thomas Himmler, Odenthal (DE); Dirk Brohm, Mettmann (DE); Wahed Ahmed Moradi, Monheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 17/045,939

(22) PCT Filed: Apr. 3, 2019

(86) PCT No.: PCT/EP2019/058356
§ 371 (c)(1),
(2) Date: Oct. 7, 2020

(87) PCT Pub. No.: WO2019/197232
PCT Pub. Date: Oct. 17, 2019

(65) Prior Publication Data
US 2021/0403406 A1 Dec. 30, 2021

(30) Foreign Application Priority Data
Apr. 10, 2018 (EP) .................... 18166472

(51) Int. Cl.
| C07C 51/08 | (2006.01) |
| C07C 17/16 | (2006.01) |
| C07C 29/141 | (2006.01) |
| C07C 45/42 | (2006.01) |
| C07C 253/14 | (2006.01) |
| C07F 3/02 | (2006.01) |

(52) U.S. Cl.
CPC .............. *C07C 51/08* (2013.01); *C07C 17/16* (2013.01); *C07C 29/141* (2013.01); *C07C 45/42* (2013.01); *C07C 253/14* (2013.01); *C07F 3/02* (2013.01)

(58) Field of Classification Search
CPC ....... C07C 51/08; C07C 17/16; C07C 29/141; C07C 45/42; C07C 253/14; C07C 45/516; C07C 309/66; C07C 309/73; C07C 33/46; C07C 47/56; C07C 57/30; C07C 255/35; C07C 53/19; C07F 3/02; B01J 25/02
USPC ....................................................... 562/409
See application file for complete search history.

(56) References Cited
U.S. PATENT DOCUMENTS
| 7,897,543 | B2 | 3/2011 | Bretschneider et al. |
| 8,507,688 | B2 | 8/2013 | Himmler et al. |
| 2011/0039701 | A1 | 2/2011 | Angermann et al. |

FOREIGN PATENT DOCUMENTS
| CN | 102633626 A1 | 8/2012 |
| JP | 2002513025 A | 5/2002 |
| JP | 2011512321 A | 4/2011 |
| WO | 2001/23387 A2 | 4/2001 |
| WO | 2004/050607 A1 | 6/2004 |
| WO | 2006011670 A1 | 2/2006 |
| WO | 2006/089633 A2 | 8/2006 |
| WO | 2009/045479 A1 | 4/2009 |
| WO | 2010/104217 A1 | 9/2010 |
| WO | 2011/089072 A1 | 7/2011 |
| WO | 2013/025425 A1 | 2/2013 |
| WO | 2016/071920 A2 | 5/2016 |
| WO | 2018/015489 A1 | 1/2018 |

OTHER PUBLICATIONS

Loefgren, et al., "Syntheses of three Xylocaine® Analogues, Steric Effects in the Reaction between 2,6-Dimethylphenyllithium and Epichlorohydrin," Acta Chemica Scandinavica, (1963), vol. 17: 1252-1261.
International Search Report for Application No. PCT/EP2019/058356 dated May 10, 2019.
Database Registry, Chemical Abstracts Service, 2016, Database accession No. 1879859-20-7.
Database Registry, Chemical Abstracts Service, 2016, Database accession No. 1874998-32-9.
Database Registry, Chemical Abstracts Service, 2014, Database accession No. 1601046-43-8.
Geier et al., "Effects of aldehyde or dipyrromethane substitudents on the reaction course leading to meso-substituted porphyrins" Tetrahedron, Bd. 60, Nr. 50, Oct. 18, 2004, pp. S1-S29.
Geier et al., "Effects of aldehyde or dipyrromethane substitudents on the reaction course leading to meso-substituted porphyrins" Tetrahedron, Bd. 60, Nr. 50, Oct. 18, 2004, pp. 11435-11444.
Xiang et al., "Stereoselective Synthesis of All Individual Isomeres of B-Methyl-2'-6'-dimethylphenylalanine" Tetrahedron Asymmetry, Bd. 6, Nr. 1, Jan. 1, 1995, pp. 83-86.
Xiong et al., "Novel Selective Estrogen Receptor Downregulators (SERDs) Developed against Treatment-Resistant Breast Cancer" J. Med. Chem. 2017, 60, 1325-42.
Muehlebach et al., "Aryldiones incorporating a [1,4,5]ocaduazeoabe rubgm Part I: Discovery of the novel cereal herbicide pinoxaden" Bioorg. & Med.Chem. 17 (2009) 4241-56.
Gruenberg et al., "Synthesis of Arylacetates from Benzylic Alcohols and Oxalate Esters through Decarboxylative Coupling" Chem.Eur.J. 19 (2013) 7334-7.
Padial et al., "Stabilisation of 2,6-Diarylpyridinium Cation by Through-Space Polar-π Interactions" Chem.Eur.J. 2014,20, 6268-71.

(Continued)

*Primary Examiner* — Ana Z Muresan
(74) *Attorney, Agent, or Firm* — McBee Moore & Vanik IP, LLC; Felix Pape

(57) ABSTRACT

The invention relates to a multi-stage process for preparing 2,6-dialkylphenylacetic acids of the general formula (I) by reacting 2,6-dialkylbromobenzenes with (1) magnesium, (2) a formamide, (3) an acid, (4) hydrogenation of the benzaldehyde obtained, (5) activation of the benzyl alcohol obtained, (6) cyanation of the activated benzyl alcohol and (7) hydrolysis of the nitrile obtained.

5 Claims, No Drawings

(56) References Cited

OTHER PUBLICATIONS

Wikipedia, "Bouveault aldehyde synthesi," https://en.wikipedia.org/wiki/Bouveault_aldehyde_synthesis.
Chinese Search Report for 2019800246159, dated Nov. 18, 2022.
Carruthers, W., "Modern Organic Synthesis Methods," the First Edition, Qingdao Ocean University Press, Apr. 1990, p. 425.
Li, Hui, et al., "Synthesis Research of 2,4,6-Trimethylphenylacetic Acid," Fine Chemicals Intermediates, 2010, vol. 40, Issue 1: pp. 15-17.
ACES, RN No. 2159586-57-7, ACS Database Entry, dated Dec. 17, 2017.
Zhu et al., "Synthesis of 2,4,6-Trimethylbenzaldehyde," Fine Chemical Intermediates, Jun. 2005, No. 35, vol. 3, pp. 33-34 (2 pages), with English abstract.

PROCESS FOR PREPARING 2,6-DIALKYLPHENYLACETIC ACIDS

CROSS-REFERENCE TO RELATED APPLICATIONS

This application is the National Stage entry of International Application No. PCT/EP2019/058356, filed 3 Apr. 2019, which claims priority to European Patent Application No. 18166472.3, filed 10 Apr. 2018.

BACKGROUND

Field

The present invention relates to a process for preparing 2,6-dialkylphenylacetic acids of the general formula (I).

2,6-Dialkylphenylacetic acids of the general formula (I) are important intermediates for the preparation of bioactive compounds which can be used specifically for controlling pests in crop protection. They are especially useful for the preparation of insecticidal, acaricidal or herbicidal cyclic keto-enols (for example WO 2006/089633), with the corresponding 2,6-dialkylphenylacetyl chlorides being produced from these 2,6-dialkylphenylacetic acids.

Description of Related Art

Various methods for preparing 2,6-dialkylphenylacetic acids are already known (for example Bioorg.& Med. Chem. 17 (2009) 4241-56; Chem. Eur. J. 19 (2013) 7334-7; WO 2004/050607; WO 2010/104217; US 20110039701; WO 2011/003530; WO 2011/089072; WO 2018/015489). However, these methods are not entirely satisfactory. Thus, for example, in some of these methods the yields are unsatisfactory or expensive reagents such as palladium catalysts must be used, for example, as a result of which the synthesis may become uneconomical. In addition, it is required for the production of active ingredients for the fields of pharmaceuticals or agriculture that palladium or other heavy metals be removed to very low tolerated residual amounts. The use of sensitive transition metal catalysts also necessitates the use of highly pure starting materials, since otherwise deactivation ("poisoning") of the catalyst may easily occur.

One possibility for preparing 2,6-dialkylphenylacetic acids without the use of a palladium catalyst consists for example of firstly synthesizing a 2,6-dialkylbenzaldehyde starting from a 2,6-dialkylbromobenzene; hydrogenating this aldehyde to give the corresponding 2,6-dialkylbenzyl alcohol; converting this benzyl alcohol to a corresponding 2,6-dialkylbenzyl halide; reacting the benzyl halide with an inorganic cyanide to give the corresponding 2,6-dialkylphenylacetonitrile, and subsequently hydrolysing the 2,6-dialkylphenylacetonitrile to give the 2,6-dialkylphenylacetic acid.

The preparation of the intermediate compound (4-chloro-2,6-dimethylphenyl)acetonitrile is already known (WO 2001/23387), wherein 4-chloro-2,6-dimethylbromobenzene is firstly reacted with butyllithium and then with N,N-dimethylformamide and the 4-chloro-2,6-dimethylbenzaldehyde is thus obtained; this aldehyde is reduced by means of sodium borohydride to give 4-chloro-2,6-dimethylbenzyl alcohol; this alcohol is reacted with thionyl chloride to give 4-chloro-2,6-dimethylbenzyl chloride; and subsequently this benzyl chloride is converted with sodium cyanide to (4-chloro-2,6-dimethylphenyl)acetonitrile.

However, the use of butyllithium and sodium borohydride in this process is disadvantageous, both of these being expensive and only handleable with difficulty on an industrial scale (for example low reaction temperatures of up to −100° C. in the reaction with butyllithium; Chem. Eur. J. 2013, 19, 7334-7).

It is also already known to use magnesium instead of butyllithium and thereby to prepare the corresponding 2,6-dialkylphenyl Grignard compounds (for example Chem. Eur. J. 2014, 20, 6268-71; J. Med. Chem. 2017, 60, 1325-42). Further reactions to give 2,6-dialkylphenylacetic acids are however not disclosed therein.

It is also already known (US 20110039701; WO 2010/104217) to react 2,6-dialkylphenyl Grignard compounds with paraformaldehyde in order thereby to directly prepare the corresponding benzyl alcohols and from them the corresponding benzyl chlorides. However, the fact that the benzyl alcohols prepared in this way can only be freed completely of paraformaldehyde by very expensive measures is a disadvantage of this process. This is however absolutely essential in order to avoid the formation of highly carcinogenic bis(chloromethyl) ether in the following step.

SUMMARY

Accordingly, there continues to be a need for an improved process for preparing 2,6-dialkylphenylacetic acids.

The present invention therefore involves a novel process for preparing 2,6-dialkylphenylacetic acids of the formula (I)

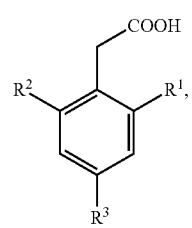

in which $R^1$ and $R^2$ independently of one another represent $C_1$-$C_6$-alkyl, and $R^3$ represents hydrogen, $C_1$-$C_6$-alkyl, fluorine or chlorine, characterized in that in a first step (1) a 2,6-dialkylbromobenzene of the formula (II)

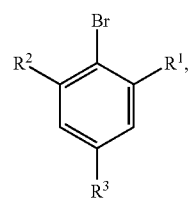

in which $R^1$, $R^2$ and $R^3$ have the definitions given above, is reacted with magnesium in the presence of a solvent to give a Grignard compound of the general formula (III),

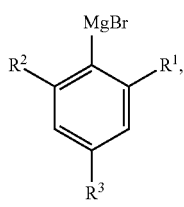

in which $R^1$, $R^2$ and $R^3$ have the meanings given above;

in a second step (2), this Grignard compound of the formula (III) is reacted with an N,N-dialkylformamide of the general formula (IV)

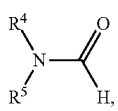

in which $R^4$ and $R^5$ independently of one another represent $C_1$-$C_6$-alkyl or together represent —$(CH_2)_2$—X—$(CH_2)_2$—, wherein X is $CH_2$, oxygen or sulfur, to give a compound of the general formula (V)

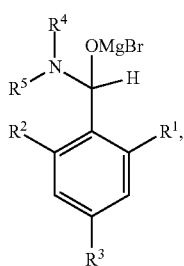

in which $R^1$, $R^2$, $R^3$, $R^4$ and $R^5$ have the definitions given above;

in a third step (3), the compound of the general formula (V) is reacted by hydrolysis under acidic conditions to give an aldehyde of the general formula (VI)

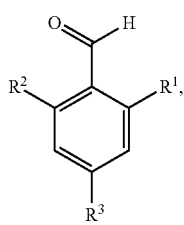

in which $R^1$, $R^2$ and $R^3$ have the definitions given above;

in a fourth step (4), the aldehyde of the general formula (VI) is hydrogenated to give a benzyl alcohol of the general formula (VII)

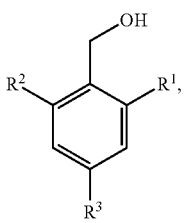

in which $R^1$, $R^2$ and $R^3$ have the definitions given above, in the presence of a catalyst;

in a fifth step (5), the benzyl alcohol of the general formula (VII) is reacted to give a compound of the general formula (VIII)

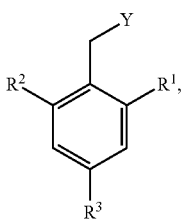

in which $R^1$, $R^2$ and $R^3$ have the definitions given above, and

Y represents chlorine, bromine, $OSO_2Me$, $OSO_2$(4-Me-Ph) or $OSO_2CF_3$, in a sixth step (6) the compound of the general formula (VIII) is reacted with a cyanide of the general formula (IX)

MCN                             (IX), in which

M represents lithium, sodium or potassium, to give a compound of the general formula (X)

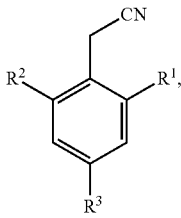

in which $R^1$, $R^2$ and $R^3$ have the definitions given above;

in a seventh step (7) the compound of the general formula (X) is hydrolysed under acidic or basic conditions to give a 2,6-dialkylphenylacetic acid of the general formula (I)

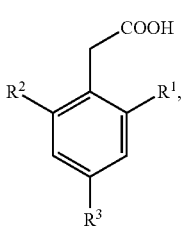

in which $R^1$, $R^2$ and $R^3$ have the definitions given above.

DETAILED DESCRIPTION OF A PREFERRED EMBODIMENT

The inventive process is depicted by Scheme 1.

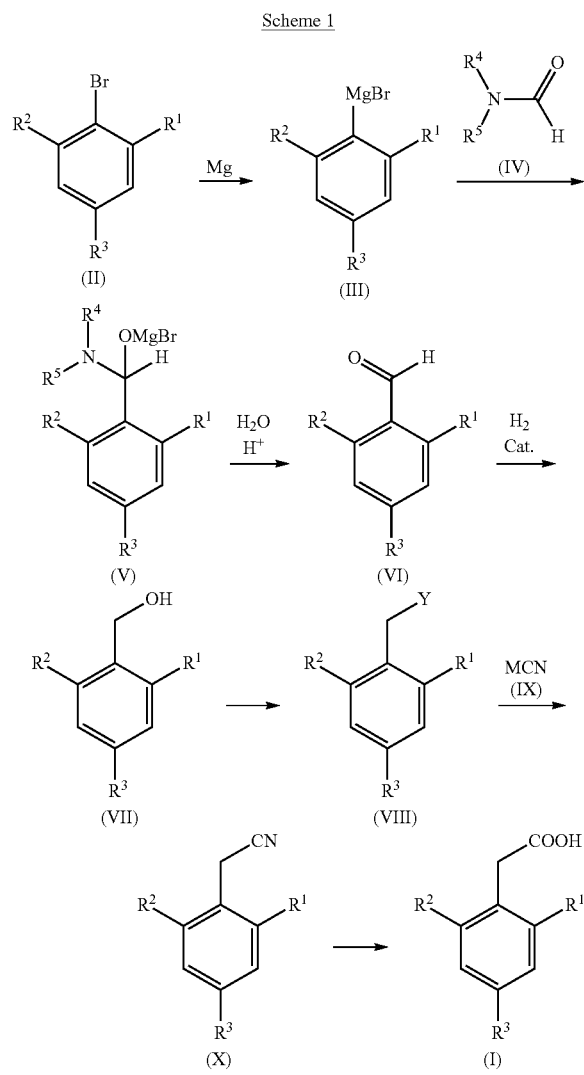

Preference is given to a process for preparing 2,6-dialkylphenylacetic acids of the formula (I), wherein $R^1$ and $R^2$ independently of one another represent $C_1$-$C_6$-alkyl, $R^3$ represents hydrogen or chlorine, $R^4$ and $R^5$ independently of one another represent $C_1$-$C_6$-alkyl or together represent —(CH$_2$)$_2$—X—(CH$_2$)$_2$—, wherein X represents CH$_2$, oxygen or sulfur, Y represents chlorine, bromine, OSO$_2$Me, OSO$_2$(4-Me-Ph) or OSO$_2$CF$_3$, M represents lithium, sodium or potassium.

Particular preference is given to a process for preparing 2,6-dialkylphenylacetic acids of the formula (I), wherein $R^1$ and $R^2$ independently of one another represent methyl or ethyl, $R^3$ represents hydrogen or chlorine, $R^4$ and $R^5$ independently of one another represent $C_1$-$C_6$-alkyl or together represent —(CH$_2$)$_2$—O—(CH$_2$)$_2$—, Y represents chlorine, bromine, OSO$_2$Me, OSO$_2$(4-Me-Ph) or OSO$_2$CF$_3$, M represents lithium, sodium or potassium.

Very particular preference is given to a process for preparing 2,6-dialkylphenylacetic acids of the formula (I), wherein $R^1$ and $R^2$ independently of one another represent methyl or ethyl, $R^3$ represents hydrogen or chlorine, $R^4$ and $R^5$ independently of one another represent methyl or n-butyl or together represent —(CH$_2$)$_2$—O—(CH$_2$)$_2$—, Y represents chlorine or bromine, M represents sodium or potassium.

Exceptional preference is given to a process for preparing 2,6-dialkylphenylacetic acids of the formula (I), wherein $R^1$ and $R^2$ represent methyl, $R^3$ represents chlorine, $R^4$ and $R^5$ represent methyl, Y represents chlorine or bromine, M represents sodium.

Likewise exceptional preference is given to a process for preparing 2,6-dialkylphenylacetic acids of the formula (I), wherein $R^1$ and $R^2$ represent methyl, $R^3$ represents hydrogen, $R^4$ and $R^5$ represent methyl, Y represents chlorine or bromine, M represents sodium.

Very particular preference is given to the preparation of (4-chloro-2,6-dimethylphenyl) acetic acid, (4-chloro-2,6-diethylphenyl) acetic acid, 2,6-dimethylphenylacetic acid and 2,6-diethylphenylacetic acid.

Emphasis is given to the preparation of (4-chloro-2,6-dimethylphenyl)acetic acid and 2,6-dimethylphenylacetic acid.

The present invention likewise provides novel compounds of the general formula (V)

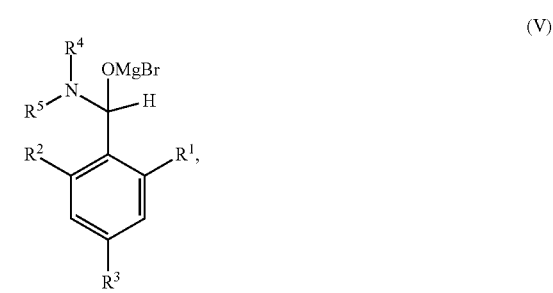

in which $R^1$, $R^2$, $R^3$, $R^4$ and $R^5$ have the definitions given above.

Preference is given to compounds of the general formula (V) in which $R^1$ and $R^2$ independently of one another represent $C_1$-$C_6$-alkyl, $R^3$ represents hydrogen or chlorine, and $R^4$ and $R^5$ independently of one another represent $C_1$-$C_6$-alkyl or together represent —(CH$_2$)$_2$—X—(CH$_2$)$_2$—, wherein X represents CH$_2$, oxygen or sulfur.

Particular preference is given to compounds of the general formula (V) in which
$R^1$ and $R^2$ independently of one another represent methyl or ethyl,
$R^3$ represents hydrogen or chlorine, and
$R^4$ and $R^5$ independently of one another represent $C_1$-$C_6$-alkyl or together represent —$(CH_2)_2$—O—$(CH_2)_2$—.

Very particular preference is given to compounds of the general formula (V) in which
$R^1$ and $R^2$ independently of one another represent methyl or ethyl,
$R^3$ represents hydrogen or chlorine, and
$R^4$ and $R^5$ independently of one another represent methyl or n-butyl or together represent —$(CH_2)_2$—O—$(CH_2)_2$—.

Exceptional preference is given to the compound of the general formula (V) in which
$R^1$ and $R^2$ represent methyl,
$R^3$ represents chlorine, and
$R^4$ and $R^5$ represent methyl.

Likewise exceptional preference is given to the compound of the general formula (V) in which
$R^1$ and $R^2$ represent methyl,
$R^3$ represents hydrogen, and
$R^4$ and $R^5$ represent methyl.

The following compound of the formula (V), in which $R^1$ and $R^2$ represent methyl, $R^3$ represents hydrogen and $R^4$ and $R^5$ represent methyl, is already known from the prior art (Tetrahedron, 60(50), 11435-11444, 2004; Tetrahedron Asymmetry, 6(3), 83-86, 1995).

This compound is therefore excluded from the scope of protection.

The present invention likewise provides novel compounds of the general formula (VIII)

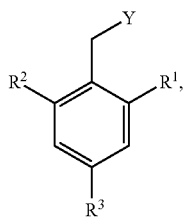

(VIII)

in which $R^1$, $R^2$ and $R^3$ have the definitions given above, and
Y represents $OSO_2Me$, $OSO_2$(4-methylphenyl) or $OSO_2CF_3$.

Preference is given to compounds of the general formula (VIII) in which
$R^1$ and $R^2$ independently of one another represent methyl or ethyl,
$R^3$ represents hydrogen or chlorine, and
Y represents $OSO_2Me$, $OSO_2$(4-methylphenyl) or $OSO_2CF_3$.

Particular preference is given to compounds of the general formula (VIII) in which
$R^1$ and $R^2$ represent methyl,
$R^3$ represents hydrogen or chlorine, and
Y represents $OSO_2Me$, $OSO_2$(4-methylphenyl) or $OSO_2CF_3$.

Very particular preference is given to compounds of the general formula (VIII) in which
$R^1$ and $R^2$ represent methyl,
$R^3$ represents chlorine, and
Y represents $OSO_2Me$, $OSO_2$(4-methylphenyl) or $OSO_2CF_3$.

Likewise very particular preference is given to compounds of the general formula (VIII) in which
$R^1$ and $R^2$ represent methyl,
$R^3$ represents hydrogen, and
Y represents $OSO_2Me$, $OSO_2$(4-methylphenyl) or $OSO_2CF_3$.

The following compounds of the formula (VIII) are already known from the prior art (WO 2009/045479, Chemcats 1879859-20-7, Chemcats 1874998-32-9, Chemcats 1601046-43-8):

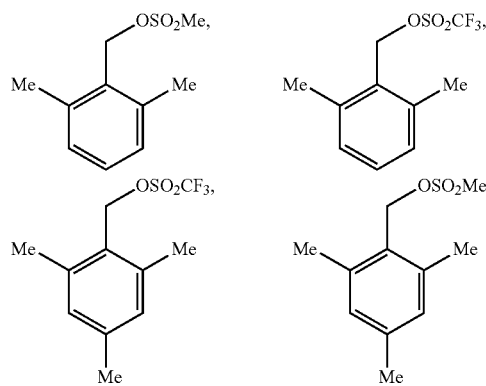

These compounds are therefore excluded from the scope of protection.

In the formulae (I), (II), (III), (IV), (V), (VI), (VII), (VIII), (IX) and (X), $R^1$, $R^2$, $R^3$, $R^4$, $R^5$, Y and M have the definitions given above.

The compounds of the formulae (II), (III), (IV), (VI), (VII), (IX) and (X) are either commercially available or can be prepared according to known processes.

General Description of the Process According to the Invention:

First Step (1) of the Process According to the Invention:

In the first step of the process according to the invention, the following may for example be used as solvent and diluent: Methyl tert-butyl ether, cyclopentyl methyl ether, tert-amyl methyl ether, 1,2-dimethoxyethane, diethylene glycol diethyl ether, tetrahydrofuran, 2-methyltetrahydrofuran, 1,4-dioxane, toluene, o-xylene, m-xylene, p-xylene or mesitylene or mixtures of these solvents and diluents.

Preference is given, as solvents and diluents, to methyl tert-butyl ether, cyclopentyl methyl ether, tetrahydrofuran, 2-methyltetrahydrofuran or toluene or mixtures of these solvents and diluents.

Particular preference is given to mixtures of tetrahydrofuran and toluene.

The amount of magnesium based on the bromoaromatic compounds of the general formula (II) is between 0.9 and 1.5 mol per mole; preferably between 1.0 and 1.3 mol per mole.

The reaction between the magnesium and the bromoaromatic compound of the general formula (II) to prepare the Grignard compound of the general formula (III) may be started in various ways known in principle, for example by addition of substoichiometric amounts of iodine, methyl iodide, ethyl iodide, 1,2-dibromoethane, trimethylsilyl chloride, solutions of methyl magnesium chloride, methyl magnesium bromide, ethyl magnesium chloride, ethyl magnesium bromide, or an already available solution of the Grignard compound of the general formula (III). Use is preferably made of iodine, 1,2-dibromoethane, ethyl magnesium bromide and an already available solution of the Grignard compound of the general formula (III). Use is particularly preferably made of ethyl magnesium bromide and an already available solution of the Grignard compound of the general formula (III).

The reaction temperature in the first step (1) of the inventive process is between 10 and 70° C., preferably between 10 and 40° C.

The product of the first step is not isolated but rather is used as a solution in the second step of the inventive process.

Second Step (2) of the Process According to the Invention:

The Grignard compound of the general formula (III) is reacted with a formamide of the general formula (IV) such as N,N-dimethylformamide, N,N-diethylformamide, N,N-dibutylformamide, N-formylpiperidine, N-formylmorpholine or N-formylthiomorpholine. Use is preferably made of N,N-dimethylformamide, N,N-dibutylformamide or N-formylmorpholine.

The amount of formamide of the general formula (IV) is between 0.9 and 2 mol per mole of the Grignard compound of the general formula (III), preferably between 1 and 1.5 mol per mole.

Naturally, the solvent and diluent used in the second step of the inventive process is the one that was used in the first step.

The reaction temperature is between 10 and 70° C., preferably between 10 and 40° C.

The product of the second step is not isolated but rather is used as a solution or suspension in the third step.

Third Step (3) of the Process According to the Invention:

Naturally, the solvent and diluent used in the third step of the inventive process is the one that was used in the first and second steps.

For the hydrolysis of the compound of the general formula (V), various acids in a mixture with water may be used, for example: hydrochloric acid, sulfuric acid, phosphoric acid, citric acid or acetic acid. Use is preferably made of hydrochloric acid or sulfuric acid.

The reaction temperature is between 10 and 70° C., preferably between 20 and 50° C.

The work-up is carried out according to known methods of organic chemistry, such as filtration, phase separation, extraction and distillation.

Fourth Step (4) of the Process According to the Invention:

In the fourth step of the process according to the invention, the following may for example be used as solvent and diluent: ethers, such as methyl tert-butyl ether, cyclopentyl methyl ether, tert-amyl methyl ether, 1,2-dimethoxyethane, diethylene glycol diethyl ether, tetrahydrofuran, 2-methyltetrahydrofuran, 1,4-dioxane; nitriles such as acetonitrile or butyronitrile; esters such as methyl acetate or butyl acetate; hydrocarbons such as hexane, methylcyclohexane, heptane, toluene, o-xylene, m-xylene, p-xylene, mesitylene or chlorobenzene; alcohols such as methanol, ethanol, propanol, isopropanol or butanol; or mixtures of these solvents and diluents.

It is also possible to carry out the hydrogenation at temperatures above the melting points of the compounds of the general formulae (VI) and (VII) without the presence of a solvent or diluent.

Preference is given, as solvents and diluents, to methanol, ethanol, tetrahydrofuran, 2-methyltetrahydrofuran, methyl acetate or mixtures of these solvents and diluents, and also to carrying out at temperatures above the melting points of the compounds of the general formulae (VI) and (VII) without the presence of a solvent or diluent.

As catalysts in the fourth step of the inventive process, use may in principle be made of all those that are suitable for the hydrogenation of a benzaldehyde to give the corresponding benzyl alcohol, for example catalysts with the metals palladium, platinum, iridium, rhodium, ruthenium, cobalt or nickel. Preference is given to catalysts with the metal ruthenium, cobalt or nickel.

The hydrogenation may be carried out both with homogeneously dissolved catalysts and with heterogeneous catalysts. Examples include: cobalt sponge catalyst (Raney cobalt), nickel sponge catalyst (Raney nickel), palladium on carbon, platinum on carbon, ruthenium on carbon, {bis[2-(diphenylphosphino)ethyl]amine}carbonylchlorohydridoruthenium(II) (Ru-MACHO, CAS 1295649-40-9), dichlorotriphenylphosphine[bis(2-(ethylthio)ethyl)amine]ruthenium (II) (CAS 1462397-86-9), [2-(aminomethyl)pyridine](dichloro)(diphenylphosphinobutane)ruthenium (II) (CAS 850424-32-7), chloro[N-[(1R,2R)-1,2-diphenyl-2-[[3-(η6-phenyl)propyl]amino-κN]ethyl]-4-methylbenzenesulfonamidato-κN]ruthenium (CAS 1192620-83-9).

The reaction temperature is between 20 and 200° C., preferably between 50 and 150° C.

The hydrogenation can be carried out at standard pressure or at elevated pressure. Preference is given to working at elevated pressure of 1 to 100 bar of hydrogen, particularly preferably 10 to 50 bar of hydrogen.

The work-up is carried out according to known methods of organic chemistry, such as filtration, phase separation, extraction and distillation.

Fifth Step (5) of the Process According to the Invention:

In the fifth step of the process according to the invention, the following may for example be used as solvent and diluent: ethers, such as methyl tert-butyl ether, cyclopentyl methyl ether, tert-amyl methyl ether, 1,2-dimethoxyethane, diethylene glycol diethyl ether, tetrahydrofuran, 2-methyltetrahydrofuran, 1,4-dioxane; nitriles such as acetonitrile or butyronitrile; esters such as methyl acetate or butyl acetate; amides such as N,N-dimethylformamide, N,N-dimethylacetamide or N-methylpyrrolidone; hydrocarbons such as hexane, methylcyclohexane, heptane, toluene, o-xylene, m-xylene, p-xylene, mesitylene or chlorobenzene or mixtures of these solvents and diluents. Preference is given to methylcyclohexane, heptane, toluene, xylene or chlorobenzene or mixtures of these solvents and diluents.

Compounds of the general formula (VIII) where Y is bromine may be obtained by methods of organic chemistry known in principle by reacting the compounds of the general formula (VII) with brominating agents such as hydrogen bromide, N-bromosuccinimide, phosphorus tribromide or thionyl bromide. Use is preferably made of hydrogen bromide or thionyl bromide.

Compounds of the general formula (VIII) where Y is chlorine may be obtained by methods of organic chemistry known in principle by reacting the compounds of the general formula (VII) with chlorinating agents such as hydrogen chloride, N-chlorosuccinimide, phosphorus trichloride, cyanuric trichloride, phosgene or thionyl chloride. Use is preferably made of hydrogen chloride, phosgene or thionyl chloride.

When preparing the compounds of the general formula (VIII) where Y is chlorine using hydrogen chloride, phosgene or thionyl chloride, in order to achieve a high yield it is preferable to initially charge the chlorinating agent and to meter the benzyl alcohol of the general formula (VII) into said chlorinating agent. It is particularly preferable to initially charge thionyl chloride and to meter the benzyl alcohol of the general formula (VII) into said thionyl chloride.

Compounds of the general formula (VIII) where Y is $OSO_2Me$, $OSO_2(4\text{-Methylphenyl})$ or $OSO_2CF_3$ may be prepared by methods of organic chemistry known in principle by reacting the compounds of the general formula (VII) with the corresponding sulfonyl chlorides or sulfonyl anhydrides.

Sixth Step (6) of the Process According to the Invention:

In the sixth step of the process according to the invention, the following may for example be used as solvent and diluent: ethers, such as methyl tert-butyl ether, cyclopentyl methyl ether, tert-amyl methyl ether, 1,2-dimethoxyethane, diethylene glycol diethyl ether, tetrahydrofuran, 2-methyltetrahydrofuran, 1,4-dioxane; nitriles such as acetonitrile or butyronitrile; esters such as methyl acetate or butyl acetate; amides such as N,N-dimethylformamide, N,N-dimethylacetamide or N-methylpyrrolidone; hydrocarbons such as hexane, methylcyclohexane, heptane, toluene, o-xylene, m-xylene, p-xylene, mesitylene or chlorobenzene; water, or mixtures of these solvents and diluents. Preference is given to methylcyclohexane, heptane, toluene, o-xylene, m-xylene, p-xylene, chlorobenzene or water or mixtures of these solvents and diluents.

Lithium cyanide, sodium cyanide or potassium cyanide may be used as cyanating agent of the general formula (IX). Use is preferably made of sodium cyanide or potassium cyanide.

The amount of cyanide used is between 0.9 and 2 mol per mole of the compound of the general formula (VIII), preferably between 1 and 1.5 mol per mole.

If the reaction takes place in a two-phase mixture of solvents and diluents, it is generally carried out in the presence of a phase transfer catalyst. Such phase transfer catalysts may for example be tetraalkylammonium salts, such as tetrabutylammonium bromide, tetraoctylammonium chloride or tetradecylammonium chloride, or mixtures of such tetraalkylammonium salts, such as Aliquat336.

The amount of phase transfer catalyst is between 0.01 and 10 mol percent, based on the compound of the general formula (VIII), preferably between 0.1 and 5 mol percent.

The reaction temperature is between 20 and 200° C., preferably between 50 and 150° C.

The reaction can also be carried out at reduced or elevated pressure.

The work-up is carried out according to known methods of organic chemistry, such as filtration, phase separation, extraction and distillation.

Seventh Step (7) of the Process According to the Invention:

In the seventh step of the process according to the invention, the following may for example be used as solvent and diluent: hydrocarbons such as hexane, methylcyclohexane, heptane, toluene, o-xylene, m-xylene, p-xylene, mesitylene or chlorobenzene; alcohols such as methanol, ethanol, n-propanol, isopropanol, butanol, ethylene glycol, diethylene glycol, triethylene glycol; water or mixtures of these solvents and diluents. Preference is given to methanol, ethanol, n-propanol, isopropanol, butanol, ethylene glycol, toluene, o-xylene, m-xylene, p-xylene, mesitylene or water or mixtures of these solvents and diluents.

If the reaction takes place in a two-phase mixture of solvents and diluents, it is generally carried out in the presence of a phase transfer catalyst. Such phase transfer catalysts may for example be tetraalkylammonium salts, such as tetrabutylammonium bromide, tetraoctylammonium chloride or tetradecylammonium chloride, or mixtures of such tetraalkylammonium salts, such as Aliquat336.

The seventh step of the inventive process may be carried out in principle under acidic or alkaline conditions.

In order to carry it out under acidic conditions, use is made of acids such as hydrochloric acid, sulfuric acid or phosphoric acid in a mixture with water. Use is preferably made of sulfuric acid in a mixture with water.

In order to carry it out under alkaline conditions, use is made of bases such as lithium hydroxide, sodium hydroxide, potassium hydroxide or calcium hydroxide. Use is preferably made of sodium hydroxide or potassium hydroxide.

The reaction temperatures are between 50 and 250° C., preferably between 80 and 200° C.

The reaction can also be carried out at reduced or elevated pressure.

The work-up is carried out according to known methods of organic chemistry, such as filtration, phase separation, extraction and distillation.

The present invention will be illustrated in more detail by the examples below, without any intention of it being limited thereto.

EXAMPLES

Example 1:
(4-chloro-2,6-dimethylphenyl)magnesium bromide

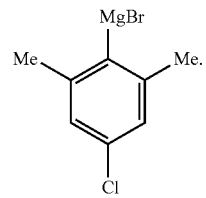

2.67 g [109.9 mmol] of magnesium turnings and a small crystal of iodine are initially charged in a 250 ml three-necked flask under argon. The flask contents are heated by a hot air gun, with stirring, until iodine vapour is visible. Approximately 10 ml of a solution of 21.7 g [99 mmol] of 4-chloro-2,6-dimethylbromobenzene in 100 ml tetrahydrofuran (THF) are added thereto and heated to 50° C. until the start of reaction becomes discernible. The remaining reactant solution is then slowly metered in, with the internal temperature being kept at 50° C. by cooling. Stirring is subsequently continued for a further hour.

Example 2:
(4-chloro-2,6-dimethylphenyl)magnesium bromide

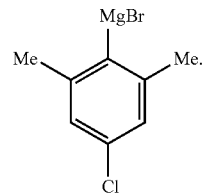

20.05 g [0.825 mol] of magnesium turnings are initially charged in a 2 l jacketed vessel under argon. Firstly, 50 ml of the solution from example 1 are added thereto at 25° C., and then 25 g of a solution of 164.6 g [0.75 mol] of 4-chloro-2,6-dimethylbromobenzene in 565 ml THF are added thereto. The start of the reaction is clear by the exothermy. The remaining amount of the reactant solution is then metered in within 2.5 hours such that the internal temperature does not exceed 33° C. At the end, further stirring is then carried out at 35° C. for one hour. Stirring a small batch sample into a THF solution of iodine and subsequent HPLC analysis shows complete conversion of the 4-chloro-2,6-dimethylbromobenzene.

Example 3: (4-chloro-2,6-dimethylphenyl)(dimethylamino)methoxide magnesium bromide

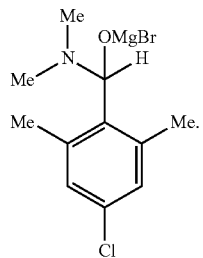

A solution of 54.8 g [0.75 mol] of N,N-dimethylformamide (DMF) in 185 ml of THF is metered in to the solution from example 2 in a 2 l jacketed vessel at 27-35° C. within approximately one hour. Stirring is subsequently continued for a further hour at 27-35° C. The product obtained is used in the next step without further work-up.

Example 4: 4-chloro-2,6-dimethylbenzaldehyde

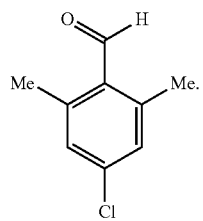

402 g of semiconcentrated hydrochloric acid are metered into the reaction mixture from example 3 in a 2 l jacketed vessel at 15° C. so that the pH drops to 1. The reaction mixture is emptied, the phases are separated, the aqueous phase is extracted three times with in each case 200 ml of methyl tert-butyl ether (MBTE), the combined organic phases are washed with 100 ml of saturated aqueous sodium chloride solution, drying is carried out over sodium sulfate and concentration is carried out under reduced pressure. 131.5 g of yellowish solid are obtained. After removal of the low-boiling impurities at 100° C. and 6 mbar, 123.4 g of yellowish solid remain which contains 90.7% of the title compound according to GC analysis, which corresponds to a yield of 83% of theory, based on the starting material in example 2.

GC/MS: m/e=167 ((M-1)+, $^{35}$Cl, 100%), 139 (M-29, 45%).

$^1$H-NMR (600 MHz, CDCl$_3$): δ=2.59 (s, 6H), 7.09 (s, 2H), 10.55 (s, 1H) ppm.

Melting point: 59° C.

Example 5: 4-Chloro-2,6-dimethylbenzyl alcohol

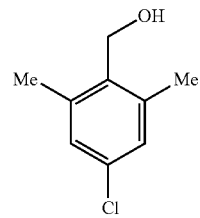 [SMILES: Cc1cc(Cl)cc(C)c1CC#N]

120.8 g of 4-chloro-2,6-dimethylbenzaldehyde with a purity of 89.2% [0.639 mol] in 480 ml of ethanol are initially charged in a 2 l autoclave. 3.6 g of Raney cobalt (Actimet: in each case washed three times with water and ethanol) are added thereto, the autoclave is closed, flushed twice with argon and hydrogenation is then carried out for 16 hours at 100° C. and 30 bar of hydrogen pressure. After cooling to room temperature and venting, the reaction mixture is filtered through Celite and the filtrate is concentrated under reduced pressure. 115.6 g of product are obtained which consists of 90.4% of the title compound according to quantitative $^1$H-NMR, which corresponds to a yield of 95.8% of theory.

GC/MS: m/e=170 (M$^+$, $^{35}$Cl, 35%), 152 (M-18, $^{35}$Cl, 100%).

$^1$H-NMR (600 MHz, d$_6$-DMSO): δ=2.34 (s, 6H), 4.44 (d, J=5.3 Hz, 2H), 4.75 (t, J=5.3 Hz, 1H), 7.06 (s, 2H) ppm.

Melting point (on 98.3% purified compound): 110.6° C.

Example 6: 4-Chloro-2,6-dimethylbenzyl alcohol

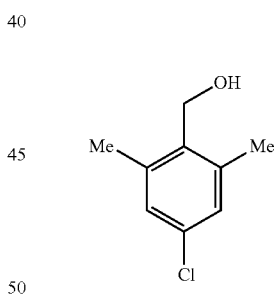

A solution of 1 g of 4-chloro-2,6-dimethylbenzaldehyde with a purity of 94% in 10 ml of tetrahydrofuran is added to an autoclave and 8 mg of [2-(aminomethyl)pyridine](dichloro)(diphenylphosphinobutane)ruthenium (II) (CAS 850424-32-7) and 16 µl of a 1.7 M solution of potassium tert-butoxide in THF are added thereto. The autoclave is flushed twice with 10 bar argon and 50 bar of hydrogen is then applied thereto for 18 hours at 50° C. After cooling to room temperature and venting, the title compound is obtained with a purity of 91.7% according to GC/MS analysis.

GC/MS: m/e=170 (M$^+$, $^{35}$Cl, 35%), 152 (M-18, $^{35}$Cl, 100%).

Example 7:
2-(Bromomethyl)-5-chloro-1,3-dimethylbenzene

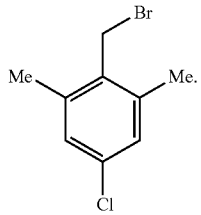

8.53 g [50 mmol] of 4-chloro-2,6-dimethylbenzyl alcohol in 60 ml of 48% strength aqueous hydrobromic acid are heated for 4 hours at 92° C. The reaction mixture is cooled to room temperature and 50 ml of methylene chloride are added thereto. The phases are separated and the aqueous phase is extracted twice with 50 ml of methylene chloride each time. The combined organic phases are extracted by shaking with 50 ml of water and then 30 ml of saturated sodium bicarbonate solution, dried over sodium sulfate, and concentrated under reduced pressure. This gives 12.22 g of a solid which, according to GC/MS analysis, contains 91.1% of the title compound, which corresponds to a yield of 95.3% of theory.

GC/MS: m/e=232 (M$^+$, $^{35}$Cl, $^{79}$Br, 5%), 153 (M-79, 100%).

Example 8:
2-(Chloromethyl)-5-chloro-1,3-dimethylbenzene

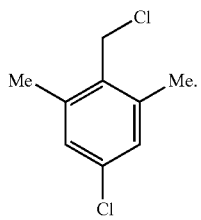

14.94 g [0.19 mol] of thionyl chloride are initially charged, heated to 72° C. and a warm (74° C.) solution of 16.47 g [0.0965 mol] of 4-chloro-2,6-dimethylbenzyl alcohol in 75 ml of toluene are added dropwise thereto within an hour. Further stirring is subsequently carried out for 90 minutes at 72° C. The excess thionyl chloride is distilled off, the residue is filtered over some Celite and concentrated under reduced pressure. This gives 20.21 g of a greenish solid which, according to GC/MS analysis, contains 87.2% of the title compound, which corresponds to a yield of 96.5% of theory.

GC/MS: m/e=188 (M$^+$, $^{35}$Cl, 12%), 153 (M-35, 100%), 119 (M-36, 72%).

$^1$H-NMR (600 MHz, CDCl$_3$): δ=2.33 (s, 6H), 4.53 (s, 2H), 6.97 (s, 2H) ppm.

Melting point: 63.5-64° C.

Example 9:
(4-Chloro-2,6-dimethylphenyl)acetonitrile

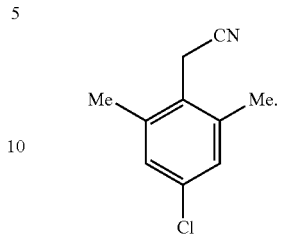

A solution of 70.8 g of 2-(chloromethyl)-5-chloro-1,3-dimethylbenzene of a purity of 74.4% is initially charged in 105 ml of toluene, 35 ml of water and 1.13 g of Aliquat336 are added thereto, the mixture is heated to 65° C. and a solution of 16.38 g [0.334 mol] of sodium cyanide in 55 ml of water is metered thereinto with vigorous stirring. Stirring is subsequently carried out for 16 hours at 80° C. The phases are separated at room temperature, the organic phase is washed with 120 ml of saturated aqueous sodium bicarbonate solution and two times 100 ml of water, drying is carried out over sodium sulfate and concentration is carried out under reduced pressure. This gives 61.9 g of a solid which, according to quantitative $^1$H-NMR, contains 69.8% of the title compound, which corresponds to a yield of 86.3% of theory. Recrystallization from 100 ml of isopropanol gives 33.1 g of a solid which, according to GC/MS analysis, contains 99.2% of the title compound, which corresponds to a yield of 65.6% of theory.

GC/MS: m/e=179 (M$^+$, $^{35}$Cl, 57%), 152 (M-27, 100%), 144 (70%), 118 (90%).

$^1$H-NMR (600 MHz, d$_6$-DMSO): δ=2.34 (s, 6H), 3.89 (s, 2H), 7.2 (s, 2H) ppm.

Melting point: 87.6° C.

Example 10: (4-Chloro-2,6-dimethylphenyl)acetic acid

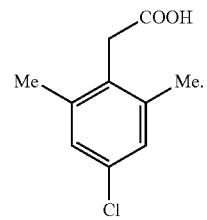

28.1 g of (4-chloro-2,6-dimethylphenyl)acetonitrile of a purity of 82% and 45.6 g of (4-chloro-2,6-dimethylphenyl)acetonitrile of a purity of 84.8% are initially charged in 300 ml of ethanol, 122 g of 45% sodium hydroxide solution are added thereto and stirring is carried out for 48 h under reflux. After cooling to room temperature, the reaction mixture is placed on ice and adjusted to a pH of 1 with concentrated hydrochloric acid, the solid is suctioned off, washed with water and dried. This gives 76.04 g of solid which, according to quantitative $^1$H-NMR, has a purity of 86.8%, which corresponds to a yield of 96.8% of theory.

GC/MS: m/e=198 (M$^+$, $^{35}$Cl, 23%), 153 (M-45, 100%), 115 (23%).

$^1$H-NMR (600 MHz, d$_6$-DMSO): δ=2.34 (s, 6H), 3.58 (s, 2H), 7.1 (s, 2H) ppm.

Melting point (after recrystallization): 188.7° C.

Example 11: (2,6-dimethylphenyl)magnesium bromide

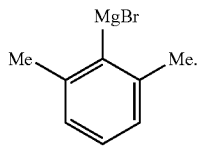

4.01 g [165 mmol] of magnesium turnings and a small crystal of iodine are initially charged in a 250 ml three-necked flask under argon. The flask contents are heated by a hot air gun, with stirring, until iodine vapour is visible. Approximately 10 ml of a solution of 27.76 g [150 mmol] of 2,6-dimethylbromobenzene in 150 ml tetrahydrofuran (THF) are added thereto and heated to 50° C. until the start of reaction becomes discernible. The remaining reactant solution is then slowly metered in, with the internal temperature being kept at 50° C. by cooling. Stirring is subsequently continued for a further hour.

Example 12: (2,6-dimethylphenyl)magnesium bromide

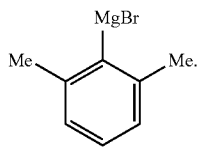

66.62 g [2.741 mol] of magnesium turnings are initially charged in a 6 l jacketed vessel under argon. Firstly, the solution from example 11 is added thereto at 25° C., and then 800 ml of THF. 100 g of a solution of 461.2 g [2.492 mol] of 2,6-dimethylbromobenzene in 1200 ml of THF are then added thereto at 30° C. The start of the reaction is clear by the exothermy. The remaining amount of the reactant solution is then metered in within 100 minutes such that the internal temperature does not exceed 33° C. At the end, further stirring is then carried out at 35° C. for two hours. Stirring a small batch sample into a THF solution of iodine and subsequent HPLC analysis shows complete conversion of the 2,6-dimethylbromobenzene.

Example 13: (2,6-dimethylphenyl)(dimethylamino)methoxide magnesium bromide

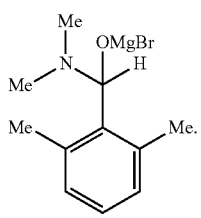

A solution of 193.1 g [2.642 mol] of DMF in 500 ml of THF is metered in to the solution from example 12 in a 6 l jacketed vessel at 24-29° C. within approximately 90 minutes. Stirring is subsequently continued for a further hour at 27° C. The product obtained is used in the next step without further work-up.

Example 14: 2,6-Dimethylbenzaldehyde

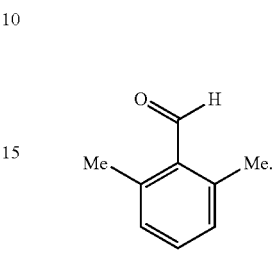

1500 g of semiconcentrated hydrochloric acid are metered in to the reaction mixture from example 13 in a 6 l jacketed vessel at 15-20° C. so that the pH drops to 1, and the mixture is stirred for a further three hours at room temperature. The reaction mixture is emptied, the phases are separated, the aqueous phase is extracted twice with in each case 500 ml of MTBE, the combined organic phases are washed with 500 ml of saturated aqueous sodium chloride solution, drying is carried out over sodium sulfate and concentration is carried out under reduced pressure. This gives 318.7 g of yellowish solid which, according to quantitative $^1$H-NMR, contains 84.0% of the title compound, which corresponds to a yield of 75.5% of theory, based on the starting material in example 12.

GC/MS: m/e=133 ((M-1)$^+$, $^{35}$Cl, 100%), 105 (M-29, 100%).

$^1$H-NMR (600 MHz, CDCl$_3$): δ=2.55 (s, 6H), 7.15 (m, 2H), 7.39 (m, 1H), 10.53 (s, 1H) ppm.

Example 15: 2,6-Dimethylbenzyl alcohol

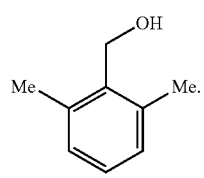

318.7 g of the compound from example 14 as a solution in 1300 ml of ethanol were initially charged in a 5 l autoclave. 3.9 g of Raney cobalt (Actimet) are added thereto, which has been washed twice with water and three times with ethanol, the closed autoclave is flushed twice with argon and hydrogenation is then carried out for 34 hours at 100° C. and 30 bar of hydrogen pressure. The reaction mixture is subsequently filtered through Celite and then concentrated under reduced pressure. This gives 299.6 g of a solid which, according to GC/MS analysis, contains 74.7% of the title compound, which corresponds to a yield of 74% of theory.

GC/MS: m/e=138 (Mt, 20%), 118 (100%).

Example 16: 2-(Chloromethyl)-1,3-dimethylbenzene

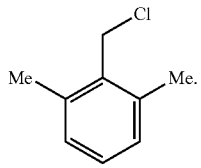

91.4 g [0.768 mol] of thionyl chloride in 100 ml of toluene are initially charged, heated to 72° C. and a solution of 100 g of 2,6-dimethylbenzyl alcohol of a purity of 74.7% in 700 ml of toluene is added dropwise thereto within an hour. Further stirring is subsequently carried out for one hour at 72° C. The excess thionyl chloride is distilled off, the residue is filtered over some Celite and concentrated under reduced pressure. This gives 107.2 g of a brown oil which, according to GC/MS analysis, contains 71.0% of the title compound, which corresponds to a yield of 89.7% of theory.

GC/MS: m/e=154 (M+, $^{35}$Cl, 17%), 119 (M-35, 100%),

Example 17: 2,6-Dimethylphenylacetonitrile

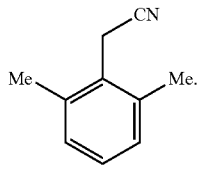

A solution of 105.6 g of 2-(chloromethyl)-1,3-dimethyl-benzene of a purity of 68.9% is initially charged in 150 ml of toluene, 50 ml of water and 1.9 g of Aliquat336 are added thereto, the mixture is heated to 65° C. and a solution of 27.68 g [0.565 mol] of sodium cyanide in 80 ml of water is metered thereinto with vigorous stirring. Stirring is subsequently carried out for 16 hours at 80° C. A further 0.85 g of Aliquat336 and 2.3 g of sodium cyanide are then added thereto and stirring is carried out for 18 hours at 80° C. The phases are separated at room temperature, the organic phase is washed with 120 ml of saturated aqueous sodium bicarbonate solution and two times 100 ml of water, drying is carried out over sodium sulfate and concentration is carried out under reduced pressure. This gives 85 g of crude product which, according to GC/MS analysis, contains 79.3% of the title compound, which corresponds to a yield of 98.6% of theory.

GC/MS: m/e=145 (M+, 40%), 118 (M-27, 100%).

Example 18: 2,6-Dimethylphenylacetic acid

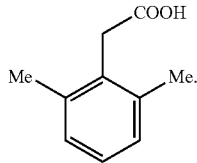

11 g of 2,6-dimethylphenylacetonitrile of a purity of 94% are initially charged in a mixture of 100 ml of triethylene glycol and 25 ml of water. 28.1 g of (85%) KOH pellets are added thereto and stirring is carried out for 18 hours at 120° C. The mixture is left to cool to 50° C., 500 ml of ice-cold water are then stirred into the reaction mixture, the reaction mixture is adjusted to a pH of 1 with 32% hydrochloric acid, the solid is filtered off, washed twice with in each case 75 ml of water, and dried. This gives 9.89 g of solid which, according to HPLC analysis, contains 96.3% of the title compound, which corresponds to a yield of 81.7% of theory.

GC/MS(sil.): m/e=236 (M+(sil.), 7%), 221 (M+(sil.)-15, 10%), 192 (10%), 119 (13%), 73(100%).

The invention claimed is:

1. A process for preparing compounds of formula (I)

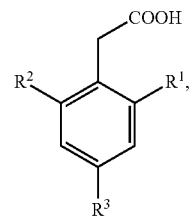

in which

R$^1$ and R$^2$ represent methyl, and

R$^3$ represents chlorine, comprising:

(1) reacting a compound of formula (II)

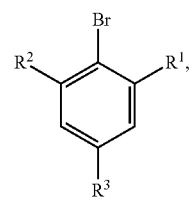

in which R$^1$, R$^2$ and R$^3$ have the definitions given above, with magnesium in the presence of a solvent to give a compound of formula (III),

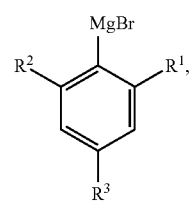

in which R$^1$, R$^2$ and R$^3$ have the meanings given above;

(2) the compound of formula (III) is reacted with a compound of formula (IV)

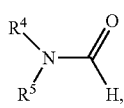  (IV)

in which
R⁴ and R⁵ represent methyl,
to give a compound of formula (V)

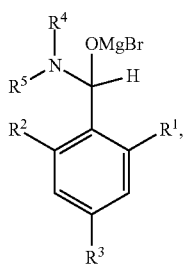  (V)

in which R¹, R², R³, R⁴ and R⁵ have the definitions given above;

(3) the compound of formula (V) is reacted by hydrolysis under acidic conditions to give a compound of formula (VI)

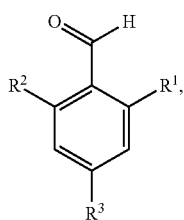  (VI)

in which R¹, R² and R³ have the definitions given above, (4) the compound of formula (VI) is hydrogenated to give a compound of formula (VII)

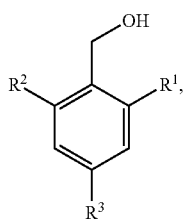  (VII)

in which R¹, R² and R³ have the definitions given above, in the presence of a catalyst;

(5) the compound of formula (VII) is reacted to give a compound of formula (VIII)

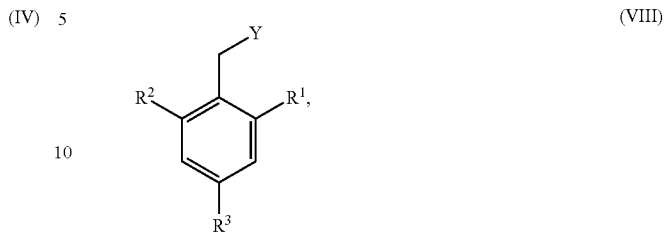  (VIII)

in which R¹, R² and R³ have the definitions given above, and
Y represents chlorine or bromine, (6) the compound of formula (VIII) is reacted with a cyanide of formula (IX)

MCN    (IX), in which
M represents sodium,
to give a compound of formula (X)

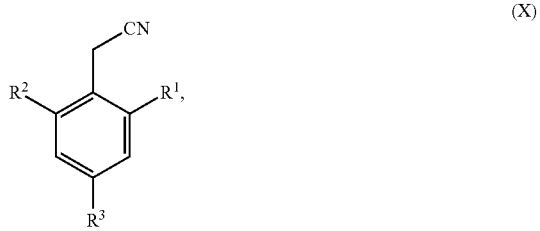  (X)

in which R¹, R² and R³ have the definitions given above;

(7) the compound of formula (X) is hydrolysed under acidic or basic conditions to give the compound of formula (I)

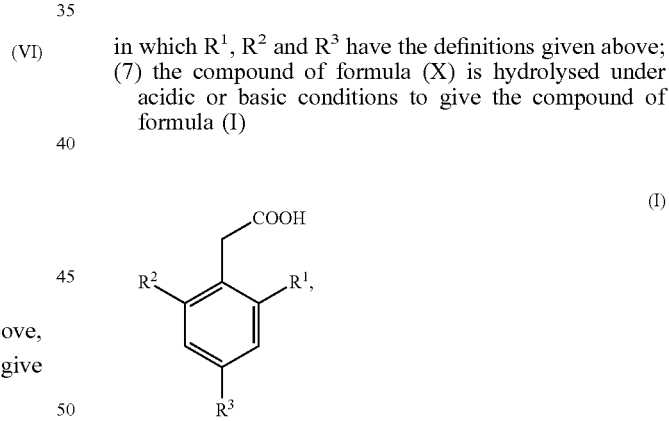  (I)

in which R¹, R² and R³ have the definitions given above.

2. The process according to claim 1, wherein, for the hydrogenation in (4), the catalyst is one or more catalysts with a metal selected from the group consisting of ruthenium, cobalt and nickel.

3. The process according to claim 1, wherein, for the hydrogenation in (4), the catalyst is Raney cobalt.

4. The process according to claim 1, wherein, for the hydrogenation in (4), the catalyst is Raney nickel.

5. The process according to claim 1, wherein, for the hydrogenation in (4), the catalyst is [2-(aminomethyl)pyridine](dichloro)(diphenylphosphinobutane)ruthenium (II).

* * * * *